United States Patent [19]

Collmann

[11] Patent Number: 4,949,366
[45] Date of Patent: Aug. 14, 1990

[54] DEVICE FOR, AND A METHOD OF, X-RAY EXAMINATION OF MOTOR VEHICLE TIRES

[75] Inventor: Wilhelm Collmann, Lübeck, Fed. Rep. of Germany

[73] Assignee: Collmann GmbH & Co. Spezialmaschinenbau KG, Lubeck, Fed. Rep. of Germany

[21] Appl. No.: 450,043

[22] Filed: Dec. 13, 1989

[30] Foreign Application Priority Data

Dec. 23, 1988 [DE] Fed. Rep. of Germany ....... 3843408

[51] Int. Cl.$^5$ .......................................... G01N 23/02
[52] U.S. Cl. ...................................... 378/61; 378/58; 378/208
[58] Field of Search ...................... 378/61, 58, 208, 91

[56] References Cited

U.S. PATENT DOCUMENTS

| | | | |
|---|---|---|---|
| 1,617,758 | 2/1927 | Heynemann | 378/61 |
| 2,301,251 | 11/1942 | Capen | 378/61 |
| 3,550,443 | 12/1970 | Sherkin | 378/61 |
| 3,621,247 | 11/1971 | Lide | 378/61 |
| 3,843,888 | 10/1974 | Fox | 378/61 |
| 3,883,744 | 5/1975 | Steffel | 378/61 |
| 4,839,914 | 6/1989 | Curry | 378/61 |

FOREIGN PATENT DOCUMENTS 2231792 6/1972 Fed. Rep. of Germany .
2262982 12/1972 Fed. Rep. of Germany .

Primary Examiner—Janice A. Howell
Assistant Examiner—Kim Chu
Attorney, Agent, or Firm—Balogh, Osann, Kramer, Dvorak, Genova & Traub

[57] ABSTRACT

A device for the X-ray examination of motor vehicle tires comprises a conveyor for conveying the tires into, and out of, an X-ray examination device, in which the tires are held in examination positions, are set in rotation and are penetrated by X-rays from within outwards thereof by means of an X-ray tube arrangement, having an X-ray receiver for observing the tire regions which have been penetrated by the X-rays, and a monitor apparatus for optical representation and evaluation of the penetrated tire regions. For improved output of examined tires the X-ray examination device comprises at least two X-ray examination units laterally adjacent to the conveyor. The X-ray receiver is constructed so as to be capable of being moved alternately from one examination unit to the other examination unit, for examination of a tire in one examination unit, while at the same time an examined tire is unloaded from the other examination unit and a fresh tire is loaded thereinto.

11 Claims, 3 Drawing Sheets

DEVICE FOR, AND A METHOD OF, X-RAY EXAMINATION OF MOTOR VEHICLE TIRES

FIELD OF THE INVENTION

This invention relates to a device for the X-ray examination of motor vehicle tires during a single revolution of each tire, the device comprising a conveyor for conveying tires into, and out of the X-ray examination device. The tires are held in said device in an examination position, are set in rotation and are penetrated by X-rays from within and outwardly by means of an X-ray tube arrangement, X-ray receiving means being arranged outside the tire for observing the regions thereof which have been so penetrated. A monitor apparatus is connected to said receiving means for optical representation and evaluation of the penetrated tire regions.

The invention also relates to a method of X-ray examination of motor vehicle tires according to which each tire is conveyed into a preliminary position, is taken therefrom and is brought into an examination position, where it is penetrated from within and outwardly thereof by means of X-rays during a single revolution of the tire. Regions thereof which have been so penetrated are observed by means of an external X-ray receiving means, electrical signals generated thereby being applied to a monitor apparatus for optical representation and evaluation of the penetrated tire which the evaluated tire is removed from the examination position and is conveyed away.

BACKGROUND OF THE INVENTION

Normally the tires are examined tire by tire, each tire being examined, being disposed in the examination position. The tire regions penetrated by the X-rays from tire bead to tire bead, are projected onto an X-ray receiver in the form of a diode line device. The signals from the diode line device are applied to a monitor apparatus on screens of which the X-rayed tire regions are reproduced for assessment by an operator. Although the individual operating steps, from initially loading the X-ray examination device with a tire to unloading the tire therefrom after the X-ray examination has been completed, can be carried out more or less briefly, the output rate of examined tires, is, nevertheless, unduly low.

SUMMARY OF THE INVENTION

An object of the invention is, therefore, to improve the said output rate, by simple and economical means.

According to one aspect of the invention, the X-ray examination device has at least two examination units provided laterally adjacent to the conveyor, the X-ray receiving means being constructed so as to be capable of being moved alternately from one examination unit to the other examination unit. The receiving means receives, X-rays from the tire regions penetrated thereby. The tire is aligned in the examination position in one examination unit, whilst at the same time an examined tire is being unloaded from the other examination unit and a new tire is being loaded thereinto.

In a method according to another aspect of the invention a first tire which is to be examined, is conveyed horizontally into a first initial position on a conveying line, is brought from this initial position into a vertical position and in that position is inserted into a first examination unit laterally adjacent to the conveying line, and is aligned therein in a vertical examination position, whilst at the same time a second tire, disposed in a second examination unit laterally adjacent to the conveying line, in a vertical examination position, is examined by means of the X-ray receiving means. Said receiving means is then moved from the second examination unit to the first examination unit and the tire is aligned in the first examination unit and is examined, whilst at the same time the previously examined second tire is returned from the second examination unit into its horizontal initial position on the conveying line and is conveyed away. A further tire to be examined is then conveyed horizontally into its initial position and is inserted into the second examination unit in a vertical position, and is aligned therein in a vertical examination position. The examined first tire is then returned from the first examination unit into its horizontal initial position on the conveying line and is conveyed away. At the same time, a further tire which is to be examined is conveyed into its initial position and the X-ray receiving means is again moved from the first examination unit to the second examination unit.

By means of the device and the method according to the invention, the throughput of examined motor vehicle tires is substantially increased, since unavoidable idle times do not, or do not substantially, impair the said throughput. Whilst, in fact, one examination unit is examining a tire, the other examination unit is being unloaded and loaded. Moreover, the device according to the invention is of simple construction, despite the provision of a plurality of examination units, since only a single X-ray receiving means is required and this can be moved from examination unit to examination unit on a simple longitudinal guideway. The tires to be examined are centrally aligned exactly and rapidly in their vertical examination positions in the respective examination units, such alignment being readily carried out because the tires are already in a vertical position when they are brought into the respective examination units.

DETAILED DESCRIPTION OF THE IGNITION

Figure 1:
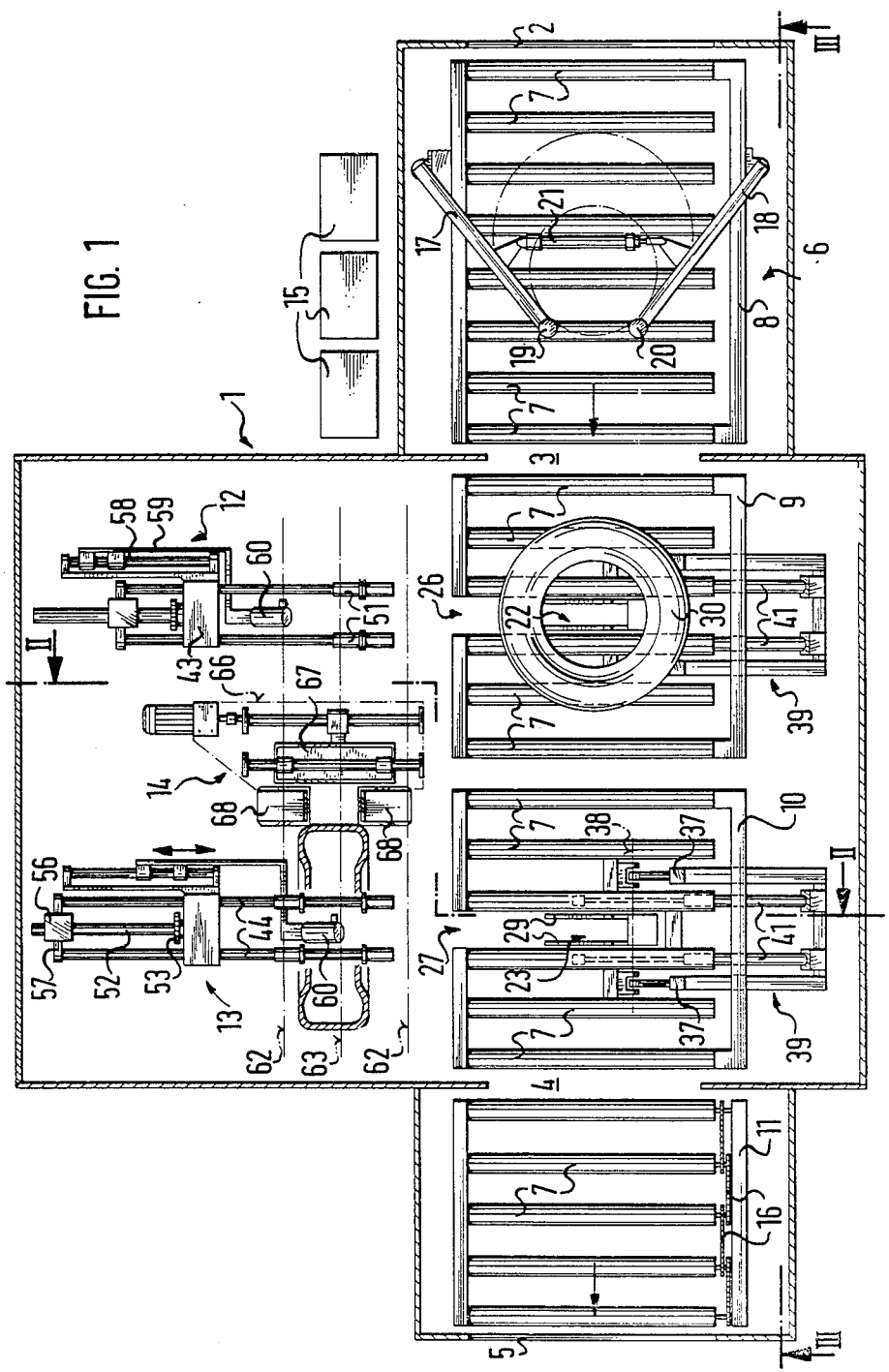
FIG. 1 is a diagrammatic plan vIew of a device for the X-ray examination of motor vehicle tires.

As shown in FIG. 1, the examination device consists of the following main structural components: a housing 1 having openings 2, 3, 4 and 5 therein; a horizontal roller conveyor 6, preferably extending rectilinearly through the housing 1, and comprising a plurality of rotatable rollers 7, providing two swivellable conveying units 9 and 10, arranged consecutively following an input section 8, and being followed by an output section 11; at least two examination units 12 and 13, arranged laterally adjacent to the swivellable conveying units 9 and 10, each for examining one motor vehicle tire, one examination unit 12 or 13 being associated with each unit 9 and 10; an X-ray receiver in the form of a diode line device 14, which is movable back and forth between the examination units 12 and 13 and parallel to the conveyor 6; and a monitor apparatus 15, consisting, for example, of three pieces of equipment, for reproducing thereon &he two sides and the tread of a tire which is being examined.

The conveyor input section 8 for conveying tires into the device and the conveyor output section 11 for conveying them away therefrom are of known construction and are therefore described herein only briefly. The rollers 7 are driven by means of a chain drive 16, which is illustrated diagrammatically in the conveyor output section 11, but which are also provided in each of the conveyor sections 8, 9 and 10. The input section 8 has an aligning unit consisting of two swivellable arms 17 and 18 provided with vertical stop elements 19 and 20 and an actuating cylinder 21, connecting the arms 17 and 18, for aligning each incoming tire centrally on the input section 8, on which are shown diagrammatically a smaller tire and a larger tire lying horizontally and having been aligned. The incoming tires are aligned by means of the aligning unit, with the longitudinal centre of the input section 8, irrespective of their diameters.

Transfer apparatus 22 and 23 are associated with the swivellable conveying units 9 and 10, respectively, each transfer apparatus 22 and 23 being movable between the units 9 and 10 and the associated examination units 12 and 13, in order each to transport one tire to the examination units, as described in detail below. The structure of the conveying units 9 and 10 and their associated transfer apparatus 22 and 23 is identical and will best be apparent from FIGS. 1 and 2.

Each swivellable unit 9 and 10 comprises a frame 24 with upper rollers 7, each of which is driven by means of its own motor powered chain drive 25. The transfer apparatus 22 and 23 engage substantially centrally in recesses 26 and 27 in the swivellable conveying units 9 and 10, said recesses running transversely of the main tire-conveying direction, whereby each recess 26 and 27 opens towards the associated examination unit 12 or 13.

Figure 2:
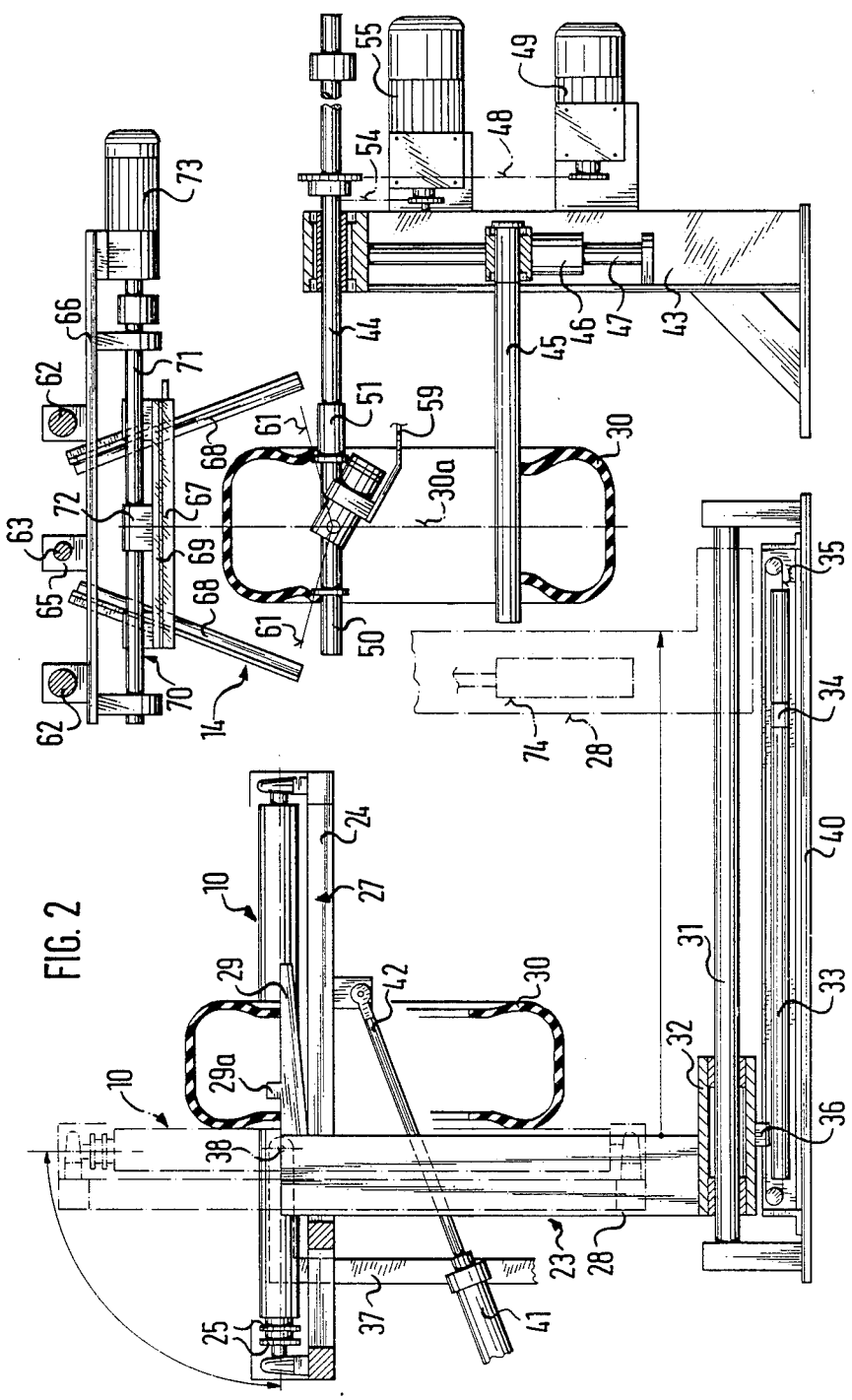
FIG. 2 is a view taken on the lines II—II in FIG. 1.

Each transfer apparatus 22 and 23 comprises a vertical stand 28, at the upper end of which is attached a horizontal tire support arm 29, pointing towards the associated examination unit 12 or 13, for receiving on the arm 29 a tire 30 (FIG. 2). Each support arm 29 is preferably constructed as two arms (FIG. 1), so that the tire in its initial position rests securely thereon. Each support arm 29 has at least one upwardly projecting stop 29a, so that a tire suspended vertically on the arm 29 does not fall therefrom when the stand 28 of the arm 29 is being moved. Each stand 28 is mounted to two fixed, horizontal guide rods 31 by means of a slider foot 32 and is driven therealong by a hydraulic piston and cylinder unit 33, the piston 34 of which cooperates with a traction cable 35, which in turn engages a connecting lug 36 of the slider foot 32.

Each conveying unit 9 and 10 is mounted to the top of a column structure 37 so as to be swivellable about a horizontal axis 38, the column structure 37 being attached to a lower frame 39, which in turn is connected to a base plate 40 supporting the respective transfer apparatus 22 or 23.

An actuating piston and cylinder unit 41 is articulated to each frame 39, the piston rod 42 of the unit 41 being articulated to the frame 24 of the associated swivellable conveying unit 9 or 10, so that the latter can be angularly oriented about the axis 38.

The examination units 12 and 13 shown in FIGS. 1 and 2 are identical in their structure, and only one of these units will therefore be described herein.

Each examination unit 12 and 13 comprises a vertical stand 43 provided with two upper, horizontal holding arms 44 and one lower, horizontal, vertically movable, holding arm 45, to receive and vertically align the tire 30. The lower holding arm 45 is vertically movable by means of a fluid cylinder 46, mounted on a vertical guide 47. The upper holding arms 44 are rotatably mounted and are driven in rotation by means of a chain drive 48 and a motor 49.

Each upper holding arm 44 has an outer, fixed support element 50 and an inner, horizontally movable support element 51, for grasping the tire 30 at its beads and precisely aligning it with its median plane 30a in a vertical, examination position. The support elements 51 may be moved horizontally in various ways, for example by means of a conventional "rolling nut drive", shown partially in FIG. 1. Such drive comprises, for example, a shaft-like component 52 on which is a chain wheel 53 driven in rotation by way of a chain 54, and a motor 55, and has a transfer member 56, which cooperates via a cross-piece 57 with the upper holding arms 44 in such a way that the support elements 51 are moved horizontally along the support arms 44.

As shown in FIG. 1, each examination unit 12 and 13 is equipped with an X-ray examination arrangement comprising a horizontal guide rod 58 attached to the respective stand 43, the rod 58 carrying a slider arm 59, on the free end of which is mounted an X-ray tube 60. The slider arm 59 is moved horizontally by means of a drive (not shown). The tube 60 is preferably a polydirectional X-ray tube for penetrating the tire from bead to bead, with X-rays 61 (as shown in FIG. 2).

Figure 3:
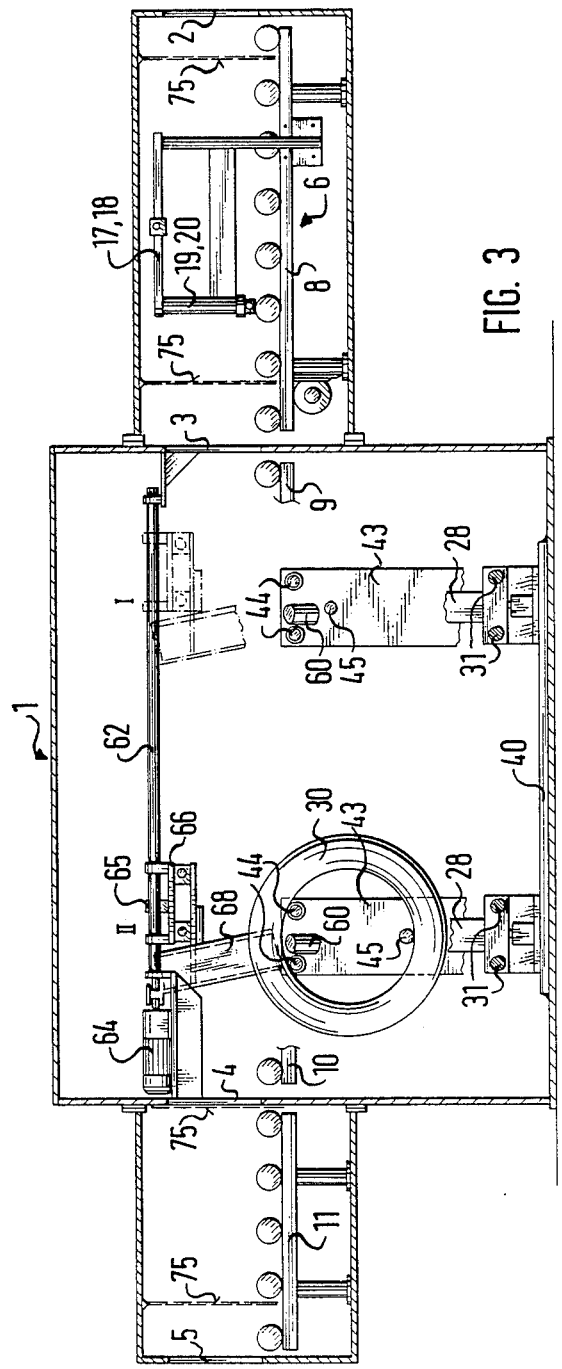
FIG. 3 is a view taken on the lines III—III in FIG. 1.

The diode line device 14, shown centrally in FIG. 1, is mounted so as to be movable above the examination units 12 and 13 on a horizontal guide arrangement, which can best be seen in FIGS. 2 and 3. As shown in FIG. 2, the guide arrangement comprises two upper guide rods 62 and a draw rod 63, for example a threaded spindle, arranged therebetween, the rod 63 being driven in rotation by means of a motor 64 and cooperating for example with a connecting member 65 screw threaded on the draw rod 63 and being attached to a support plate 66 of the diode line device 14.

The diode line device 14 comprises three line units, namely one line unit 67, for the tread of the tire 30 and two lateral line units 68, inclined for example, for the sides of the tire. The line units 67 and 68 may be of rigid construction or may be constructed so as to be adjustable with respect to each other. All of the line units 67 and 68 are attached to a plate-shaped support element 69, which in turn is adjustably mounted on a horizontal guide, which is generally referenced 70. The guide 70 may, for example, have a threaded spindle 71, cooperating with a nut element 72 of the plate 69 and with a drive motor 73, for moving the diode line units 67 and 68 horizontally, in the interest of accurate adjustment of the tire 30 (FIG. 2).

In operation, a tire 30 aligned on the conveyor input section 8 is supplied to the first swivellable conveyor unit 9 by opening the arms 17 and 18, the tire 30 being held approximately centrally of the unit 9 so that it comes to lie over the first transfer apparatus 22. The unit 9 is then swivelled downwards so that the tire 30 is received by, and is suspended vertically on, the support arm 29 of the apparatus 22. The apparatus 22 then travels to the first examination unit 12 and deposits the tire on the support arms 44 thereof by lowering the arm 29. By means of the support elements 50 and 51, the tire is precisely aligned vertically, by adjusting the elements 51 appropriately horizontally. In the meantime, the diode line device 14, which has previously examined a tire in the second examination unit 13, is moved from its position II in FIG. 3 to the first examination unit 12 (position I, FIG. 3) and the examination of the tire 30 in the first examination unit 12, in which the tire is set in rotation begins.

Immediately upon completion of the examination in the second examination unit 13, the tire examined therein is removed from the second examination unit 13 again by means of the second transfer apparatus 23 and is returned to the second swivellable conveying unit 10 and is conveyed away from there by way of the output section 11. In the meantime, a further tire is conveyed from the input section 8 by way of the first swivellable conveying unit 9 to the second swivellable conveying unit 10 and is stopped there above the second transfer apparatus 23. The apparatus 23 now takes charge of the tire again, the unit 10 being swivelled down, so that the tire is now again in a vertical initial position on the support arm 29 of the apparatus 23. The apparatus 23 now travels into the second examination unit 13, in order to position the tire on the holding arms 44, of the unit 13 after which the tire is secured in a vertical examination position as described above.

In the meantime, the examination procedure in the first examination unit 12 has been completed, so that the diode line device 14 again moves to the second examination unit 13, in order to begin the examination of the tire there.

The first transfer apparatus 22 in turn, now takes the examined tire from the first examination unit 12 and returns to its initial position. The swivellable conveying unit 9 is now swivelled back from its vertical position into its horizontal position again, so that the tire lies on the unit 9 ready to be conveyed away horizontally by way of the second conveying unit 10 and the output section 11. Whilst the examined tire is being conveyed away from the first examination unit 12, as just described, the next tire has already been conveyed to the first swivellable conveying unit 9, where the operating steps described above are repeated.

In the present embodiment the X-ray tube arrangement consists of two individual X-ray tubes, one tube being provided in each examination unit 12 and 13. Only a single X-ray tube may, however, be provided, such tube being integrated into the diode line device 14 and moved therewith. Where two X-ray tubes are employed there may be provided, only one generator for the tubes and a high-tension changeover switch for connecting the X-ray tube to be used to the generator. Each of the X-ray tubes 60 shown in FIG. 1 is adjustable according to the phase of the examination, between its operating position inside the tire and its non-operating position outside the tire as shown in FIG. 1. The head region, for example, of the stand 28 of each transfer apparatus 22 and 23 is of telescopic construction for lowering the support arm 29 of the transfer apparatus when a tire is to be inserted thereinto and for raising it when a tire is to be removed from the respective examination unit. Such telescopic construction of the stands 28 is partially illustrated in broken lines in FIG. 2 by way of a lifting cylinder 74 for raising and lowering the stand 28.

The input section 8 and the output section 11 cooperate with curtains 75 (FIG. 3), each of which consists of elongated members suspended so as to be freely movable, and having lead-in parts, for example, in the form of balls. The housing 1, in which the X-ray tubes 60 operate, is thereby externally screened against radiation. Alternatively, conventional doors may be used to this end. Instead of the diode line device 14, a conventional camera device may be provided as the X-ray receiving device.

What is claimed is:

1. A device for the X-ray examination of motor vehicle tires during a single revolution of each tire, the X-ray examination device comprising;

a first X-ray examination unit for holding the tires in a vertical examination position and rotating them, and including an X-ray tube arrangement for irradiating the tires from within and outwardly thereof, X-ray receiving means positioned for receiving X-rays outside the tires and which have penetrated regions thereof and monitor apparatus connected to said receiving means for optical representation and evaluation of said regions;

and a conveyor for conveying said tires into, and out of, said X-ray examination device;

said X-ray examination device further comprising at least one second such X-ray examination unit, said examination units being located laterally adjacent to said conveyor; means for loading tires into, and unloading them from, said examination units; means for moving the X-ray receiving means, such means being common to said units, alternately from one of said examination units to the other to receive X-rays which have penetrated said regions of a tire in said vertical examination position in one examination unit whilst said loading and unloading means is unloading a tire from, and loading a further tire into, the other examination unit.

2. An examination device, as claimed in claim 1, wherein each X-ray examination unit comprises a plurality of adjustable, horizontal arms with expansion means for precise alignment of, and retention of, a tire, in said vertical examination position.

3. An examination device as claimed in claim 1, wherein the conveyor comprises means for transporting the tires in a horizontal position and a vertically swivellable conveyor unit proximate to each of the X-ray examination units, a transfer apparatus associated with each of said conveyor units being movable horizontally between such conveyor unit and the X-ray examination unit proximate thereto for taking up a tire from said conveyor unit when swivelled into a vertical position and transferring such tire to the proximate X-ray examination unit.

4. An examination device as claimed in claim 3, wherein a recess defined by each swivellable conveyor unit extends transversely of the conveyor and opens towards the proximate X-ray examination unit, the transfer apparatus associated with said conveyor unit projecting into said recess when said conveyor unit is in a raised position.

5. An examination device as claimed in claim 4, wherein said transfer apparatus comprises a vertical stand having at least one horizontal tire support arm, and means for raising and lowering said support arm to receive a tire to be vertically supported thereon.

6. An examination device as claimed in claim 5, wherein said at least one support arm has an upwardly directed stop for said tire.

7. An examination device as claimed in claim 1, wherein the conveyor extends through the said examination device.

8. An examination device as claimed in claim 1, comprising radiation proof curtains externally screening an inlet and an outlet of the conveyor.

9. An examination device as claimed in claim 1, wherein such an X-ray tube arrangement is integrated into said X-ray receiving means.

10. An examination device as claimed in claim 1, wherein said X-ray tube arrangement comprises two X-ray tubes provided with a common generator and a high tension change-over switch for connecting said tubes alternately to said generator.

11. A method of X-ray examination of motor vehicle tires, comprising the steps of:
   conveying such a tire into an initial position;
   bringing said tire from said initial position into an examination position;
   rotating said tire, penetrating the tire from within and outwardly thereof by means of X-rays, during one revolution of the tire and observing regions of the tire, so penetrated by means of external X-ray receiving means producing output electrical signals;
   applying said output signals to a monitoring means producing an optical representation and evaluation of the penetrated regions of the tire;
   removing the tire from said examination position; and conveying away the tire;
      said method comprising the further steps of:
   conveying a first tire to be examined into a first initial horizontal position on a conveying line;
   bringing said first tire from the first initial horizontal position into a vertical position, inserting it into a first X-ray examination unit laterally adjacent to the conveying line and aligning said first tire in a vertical examination position and simultaneously examining by means of said X-ray receiving means, a second tire disposed in a vertical examination position in a second X-ray examination unit laterally adjacent to said conveying line;
   moving said receiving means from said second examination unit to said first examination unit;
   examining by means of said X-ray receiving means said first tire in said first X-ray examining unit and simultaneously removing said second tire from said second X-ray examination unit and returning it to a horizontal position on said conveying line and conveying away said second tire;
   conveying a further tire to be examined, horizontally into an initial position; bringing said further tire to a vertical position and inserting it into the second X-ray examination unit and aligning it in a vertical position therein; and
   bringing said first tire from the first X-ray examination unit into a horizontal position on said conveying line and conveying said first tire away, whilst conveying yet a further tire to be examined into an initial position and moving said X-ray receiving means from the first X-ray examination unit to the second X-ray examination unit.

* * * * *